United States Patent [19]

McGarry

[11] Patent Number: 4,618,618
[45] Date of Patent: Oct. 21, 1986

[54] COMPOUNDS AND COMPOSITIONS

[76] Inventor: Errol J. McGarry, 3 Argyll Court, Eltham North, Victoria, Australia, 3095

[21] Appl. No.: 685,617

[22] Filed: Dec. 28, 1984

Related U.S. Application Data

[63] Continuation of Ser. No. 443,737, Nov. 22, 1982.

[30] Foreign Application Priority Data

Nov. 25, 1981 [AU] Australia .............................. PF1691

[51] Int. Cl.$^4$ ................. C07D 513/04; A61K 31/425
[52] U.S. Cl. ..................................... 514/368; 548/155
[58] Field of Search ........................ 548/155; 514/368

[56] References Cited

U.S. PATENT DOCUMENTS 3,331,738 7/1967 Collins ............................ 260/465 F
3,574,227 4/1971 Rimington ......................... 424/270

Primary Examiner—Robert Gerstl
Attorney, Agent, or Firm—Cushman, Darby & Cushman

[57] ABSTRACT

The invention concerns novel compounds selected from D,L-2,3,5,6-tetrahydro-6-phenylimidazo[2,1-b]-thiazolium 4-cyano-2-iodo-6-nitrophenoxide and L-2,3,5,6-tetrahydro-6-phenylimidazo[2,1-b]thiazolium 4-cyano-2-iodo-6-nitrophenoxide. The compounds are anthelmintics effective against both nematodes and trematodes and in further embodiments the invention provides processes for the preparation of the compounds of the invention, compositions comprising as active ingredient the compounds of the invention and processes for killing helminths using the compounds of the invention.

14 Claims, No Drawings

COMPOUNDS AND COMPOSITIONS

This is a continuation of application Ser. No. 443,737 filed Nov. 22, 1982.

This invention relates to organic salts having biological activity and in particular to organic salts having anthelmintic properties, to processes for the preparation of such salts, to anthelmintic compositions containing such salts and to processes of combatting helminthiasis utilizing such salts.

D,L-2,3,5,6-Tetrahydro-6-phenylimidazo[2,1-b]thiazole, hereinafter referred to as tetramisole, and especially the laevorotarory optical isomer, hereinafter referred to as levamisole, are potent anthelmintics which have found considerable commercial success because of their efficacy in the control of intestinal nematodes and lungworm in warm-blooded animals. Part of the commercial success of tetramisole and levamisole has undoubtedly been due to the development of formulations suitable for administration by injection resulting in a considerable improvement in the ease of administration of the drug.

Many anthelmintics effective in the control of trematodes and in particular the liver fluke *Fasciola hepatica* also have been developed. Unfortunately, the majority of these compounds, and in particular the more efficacious compounds which have been developed commercially, are administered orally, usually in the form of a drench, as their insolubility has precluded the development of a formulation suitable for subcutatneous injection. However, the compound 4-cyano-2-iodo-6-nitrophenol, hereinafter referred to as nitroxynil, is one fasciolicide which is effective against both mature and immature liver fluke and which is available in a formulation suitable for administration by injection.

It is evident that a composition suitable for parenteral administration and comprising levamisole or tetramisole in combination with an effective flukicide such as nitroxynil would result in a considerable improvement in the economics of treatment of animals to control helminths by providing a means for the treatment to be carried out in one simple operation. However, the present formulations of tetramisole and levamisole which are suitable for administration by subcutaneous injection are not compatible with the formulation of nitroxynil which is suitable for administration by subcutaneous injection.

On the one hand, tetramisole and levamisole are subject to base catalysed hydrolysis and as a result both are usually supplied and administered in the form of their acid addition salts with strong inorganic acids. In the widespread application of tetramisole and levamisole throughout the world, almost universally both are supplied and used in the form of their hydrochloride or dihydrogen phosphate salts. Formulations of these salts which are suitable for administration by subcutaneous injection are disclosed in Australian Patents Nos. 440,746 and 450,030 and their equivalents.

On the other hand, the formulation of nitroxynil which has been developed for parenteral administration is a water soluble salt of nitroxynil and an amine, the commercially available product being an aqueous solution of the N-ethyl-D-glucamine salt of nitroxynil.

It has now been found possible to prepare compounds which are salts of tetramisole or levamisole and nitroxynil and which may be formulated for parenteral, dermal or oral administration to control helminths Accordingly the invention provides a compound selected from D,L-2,3,5,6-tetrahydro-6-phenylimidazo[2,1-b]thiazolium 4-cyano-2-iodo-6-nitrophenoxide and L-2,3,5,6-tetrahydro-6-phenylimidazo[2,1-b]thiazolium 4-cyano-2-iodo-6-nitrophenoxide.

For convenience the compounds provided by the present invention, that is D,L-2,3,4,5,6-tetrahydro-6-phenylimidazo[2,1-b]thiazolium 4-cyano-2-iodo-6-nitrophenoxide and L-2,3,5,6-tetrahydro-6-phenylimidazo[2,1-b]thiazolium 4-cyano-2-iodo-6-nitrophenoxide, will hereinafter referred to as the nitroxynil salt of tetramisole and the nitroxynil salt of levamisole respectively. It will be evident to those skilled in the art that the nitroxynil salt of tetramisole consists of a mixture of the nitroxynil salt of the dextrorotatory optical isomer of tetramisole, D-tetramisole, and the nitroxynil salt of the laevorotatory optical isomer of tetramisole, L-tetramisole, herein referred to as levamisole.

It is known in the art that, at least in the ruminants sheep and cattle, levamisole is approximately twice as active as tetramisole as an anthelmintic agent. That is, the laevorotatory isomer levamisole is responsible for all or most of the anthelmintic activity of tetramisole. As a result the preferred compound of the invention is the nitroxynil salt of levamisole.

The compounds of the invention may be prepared, for example, by the reaction of tetramisole or levamisole with nitroxynil in an organic solvent.

Accordingly, in a further aspect the invention provides a process for the preparation of a compound of the invention which process comprises reacting tetramisole or levamisole with nitroxynil in the presence of an organic solvent. Preferably, levamisole is reacted with nitroxynil in a polar organic solvent to give a solution of the nitroxynil salt of levamisole, part or all of the solvent is removed and the compound is recovered. In an example of a suitable process levamisole is added to a hot solution of nitroxynil in a polar organic solvent such as, for example, methanol, ethanol or acetone, the volume of the solvent is reduced by evaporation or distillation, the solution is cooled, and the compound allowed to crystallize from the solution.

The novel compounds of the invention combine the proven activity of tetramisole and levamisole against nematodes such as *Haemonchus contortus,* Ostertagia spp., Trichostrongylus spp. (e.g. *Trichostrongylus axei*), Cooperia spp. (e.g. *Cooperia oncophora*), Nematodirus spp. (e.g. *Nematodirus fillicolis*), Oesaphagostomum spp. (e.g. *Oesaphagostomum venulosum*), Strongyloides spp. (e.g. *Strongyloides pappilosus*), Bunostomum spp. (e.g. *Bunostomum trigonocephalum*), Chabertia spp. (e.g. *Chabertia ovina*), Trichuris spp. (e.g. *Trichuris ovis*) and Dictyocaulus spp. (e.g. *Dictyocaulus filaria* and *Dictyocaulus viviporus*) and the proven activity of nitroxynil against trematodes such as *Fasciola hepatica* and *Fasciola gigantica.*

Accordingly, in yet a further aspect the invention provides a process for killing internal parasites of warm blooded animals which process comprises treating the infected animal with a therapeutically effective amount of a compound of the invention.

For effective anthelmintic treatment certain dosage levels are desirable, the specific dosage depending on the compound employed and the animal being treated. In general, satisfactory efficacy is achieved when the nitroxynil salt of tetramisole is administered in a single dose at dosage levels of from about 20 to 40 milligrams of active ingredient per kilogram of animal body weight, typically around 25 mg/kg, and when the nitroxynil salt of levamisole is administered in a single dose at dosage levels of from about 10 to 25 milligrams of active ingredient per kilogram of animal body weight, typically around 12 to 17 mg/kg.

Preferably the compounds of the present invention are administered in a single efficacious parenteral dose at a time when nematode and/or trematode infection is apparent or suspected. However, the compounds of the invention may also be administered orally, preferably in a single unit oral dosage form such as a tablet, bolus, capsule or drench but also as an additive to feed, or dermally, preferably in a single unit "pour-on" dosage form.

The term "parenteral" is used herein to mean intravenous, intramuscular and subcutaneous injection. Preferably the compounds of the present invention are administered in a single efficacious dose by subcutaneous injection.

Parenteral administration of the compounds of the present invention has several advantages over prior art methods for the control of nematodes and trematodes in warm blooded animals. Clearly the compounds of the present invention offer the economic advantage of enabling both nematode infections and trematode infections in warm blooded animals to be controlled by the adminstration of a therapeutic dose in a single injection.

Parenteral administration of the compounds of the present invention also offers certain therapeutic advantages over prior art methods for the control of nematodes and trematodes in warm blooded animals. For example, when levamisole dihydrogen phosphate is administered by subcutaneous injection according to the prior art the level of levamisole in the blood quickly rises to a maximum and quickly declines. However, when the nitroxynil salt of levamisole is administered by subcutaneous injection according to the present invention the level of levamisole in the blood rises to a maximum level more slowly and, advantageously, the level of levaxisole in the blood is maintained for a longer period of time than when levamisole dihydrogen phosphate is administered.

In the process of the invention the compounds of the invention are preferably administered in the form of a composition which comprises an inert carrier.

Accordingly in a still further embodiment the invention provides a composition comprising as active ingredient a compound of the invention and a pharmaceutically acceptable carrier therefor.

The nature of compositions of the invention to be employed will be determined to a large extent by the mode of administration to the infected animal.

The compositions may be administered to the animal by parenteral dose and the invention also provides an injectable composition comprising a sterile solution containing from 5 to 70% w/w preferably 5 to 30% w/w of the active ingredient in a pharmaceutically acceptable solvent.

Suitable solvents may be chosen from pharmaceutically acceptable: alcohols such as benzyl alcohol and tetrahydrofurfuryl alcohol; ketones; esters such as ethyl lactate; amides such as N-(2-hydroxyethyl)lactamide; sulfoxides such as dimethylsulfoxide; sulfones such as sulfolane; cyclic ether derivatives; formals such as glycerol formal; hydrocarbons; perfluorinated hydrocarbons such as perfluorodecalin; glycols and glycol derivatives such as ethylene glycol, propylene glycol, ethylene glycol mono- and di- alkyl ethers, propylene glycol mono- and di- alkyl ethers, polypropylene glycols, polyethylene glycols, polypropylene glycol mono- and di- alkyl ethers, polyethylene glycol mono- and di- alkyl ethers, pyrrolidones such as N-methylpyrrolidone and poly(N-vinylpyrrolidone), silicone oils such as polymethylsiloxane, aprotic solvents such as dimethylformamide, dimethylacetamide and tetramethylurea; and mixtures thereof.

Preferred solvents for use in the compositions of the present invention include: benzyl alcohol; tetrahydrofurfuryl alcohol; ethyl lactate; N-(2-hydroxyethyl)lactamide; sulfolane; glycerol formal; propylene glycol; polyethylene glycol of average molecular weight in the range of from 100 to 600, preferably of average molecular weight 200; diethylene glycol dimethyl ether; N-methylpyrrolidone; poly(N-vinylpyrrolidone); tetramethylurea; and mixtures thereof.

A particularly preferred injectable composition comprises a sterile solution of 10 to 20% by weight of the nitroxynil salt of levamisole in polyethylene glycol of average molecular weight in the range of 200 to 400.

The injectable compositions of the invention may be prepared by dissolving the active ingredient in a pharmaceutically acceptable solvent and sterilizing the solution. Alternatively, the compositions may be prepared in situ in the pharmaceutically acceptable solvent by reacting tetramisole or levamisole with nitroxynil in the pharmaceutically acceptable solvent to give a solution of a compound of the invention in that solvent, and sterilizing the solution.

Compositions of the invention suitable for administration by application to the skin of the animal may also be formulated. Accordingly the invention also provides a liquid composition for external application to an animal said composition comprising a solution or suspension containing from 1 to 70% w/w, preferably 1 to 10% w/w of the active ingredient in a pharmaceutically acceptable liquid carrier effective in passing the active ingredient through the skin of the animal. Suitable liquid carriers include, for example, pharmaceutically acceptable hydrocarbons, ketones, esters, ethers, alcohols, amides, sulfones, sulfoxides, alkylene glycols, alkylene glycol mono- and di- alkyl ethers, polyalkylene glycols, and polyalkylene glycol mono- and di- alkyl ethers.

The compositions of the invention may be administered to those animals for which tetramisole and/or levamisole are used in the treatment of helminth infections, and particularly nematode infections, and nitroxynil is used in the treatment of helminth infections, and particularly trematode infections. Examples of such animals include sheep, cattle, pigs, goats, horses and dogs. The compositions of the invention are particularly useful in the treatment of helminth infections in sheep and cattle.

The compositions of the invention may comprise, in addition to the compounds of the invention as hereinbefore defined; one or more other pharmaceutically therapeutic agents; additives to improve the shelf life of the compositions; buffering agents; preservatives; and/or additives to prevent or reduce tissue reaction at the site of injection of parenterally administered compositions.

The invention is now illustrated by, but is not limited to, the following Examples.

EXAMPLE 1

Preparation of
L-2,3,5,6-tetrahydro-6-phenylimidazo[2,1-b]thiazolium 4-cyano-2-iodo-6-nitrophenoxide (nitroxynil salt of levamisole)

Solid L-2,3,5,6-tetrahydro-6-phenylimidazo[2,1-b]-thiazole (35.0 g; 172 mmole) was slowly added to a boiling solution of 4-cyano-2-iodo-6-nitrophenol (50.0 g; 172 mmole) in ethanol (400 ml). On completion of the addition half of the ethanol was removed by distillation and the concentrated solution was filtered hot and allowed to stand. Upon cooling the product, the nitroxynil salt of levamisole, crystallised from the solution as fine yellow needles (67.0 g; 79%), mp 129.5° C. Further product was obtained by concentration of the mother liquor. The product was characterised by infra-red spectroscopy (I.R.), proton nuclear magnetic resonance spectroscopy (P.M.R.) and mass spectrometry (M.S.).

I.R. $\nu_{MAX}$ in cm$^{-1}$ (Nujol Mull): 2620 m, 2213 m, 1598 s, 1540 s, 1456 s, 1355 m, 1345 s, 1324 m, 1260 s, 1206 m, 1156 m, 1073 w, 1045 w, 1029 w, 929 w, 894 m, 880 w, 810 w, 778 m, 716 m, 703 m.

P.M.R. δ in ppm (CDCl$_3$): 9.87 (1H, br.s); 8.10 (1H, d, J=2.2 Hz); 7.86 (1H, d, J=2.2 Hz); 7.31 (5H, s); 5.72 (1H, d of d, J$_1$=7.92 Hz, J$_2$=10.12 Hz); 4.11 (1H, t, J=10.11 Hz); 3.89–3.45 (5H, m).

M.S. m/e (%): 291 (14), 290 (100), 273 (13), 260 (6), 206 (5), 205 (25), 204 (92), 203 (53), 176 (7), 150 (6), 149 (17), 148 (96), 146 (13), 133 (6), 127 (30), 121 (14), 118 (11), 117 (72), 116 (8), 104 (24), 103 (16), 102 (11), 101 (86), 91 (10), 90 (8), 89 (30), 88 (51), 87 (6), 78 (5), 77 (25), 76 (7), 75 (9), 74 (6), 73 (83), 72 (7), 63 (15), 62 (25), 61 (15), 56 (13), 54 (6), 53 (20), 51 (14), 50 (8), 45 (15).

EXAMPLE 2

This Example demonstrates the preparation of solutions of the nitroxynil salt of levamisole suitable for parenteral administration.

(a) A solution of the nitroxynil salt of levamisole was prepared by dissolving the salt (435 parts by weight) in polyethylene glycol of average molecular weight 200 and making the solution up to 3000 parts by volume with polyethylene glycol of average molecular weight 200. The solution was filtered and divided into ampoules in quantities such as to give a suitable unit dose. The ampoules were sealed and sterilised to give a sterile solution suitable for parenteral injection.

(b) The procedure described in (a) above was repeated using 435 parts by weight of the salt, 750 parts by volume of N-methylpyrrolidone and making up to 3000 parts by volume with propylene glycol.

(c) The procedure described in (a) above was repeated using 435 parts by weight of the salt, 750 parts by volume of N-methylpyrrolidone and making up to 3000 parts by volume with polyethylene glycol of average molecular weight 200.

(d) The procedure described in (a) above was repeated using 435 parts by weight of the salt, 750 parts by volume of diglyme and making up to 3000 parts by volume with propylene glycol.

(e) The procedure described in (a) above was repeated using 435 parts by weight of the salt, 150 parts by volume of N-methylpyrrolidone and making up to 3000 parts by volume with propylene glycol.

(f) The procedure described in (a) above was repeated using 435 parts by weight of the salt, 150 parts by volume of N-methylpyrrolidone and making up to 3000 parts by volume with polyethylene glycol of average molecular weight 200.

(g) The procedure described in (a) above was repeated by dissolving 435 parts by weight of the salt and 150 parts by weight of "Kollidon" 12 PF [a poly(N-vinylpyrrolidone) having a K value of 12 and available from BASF AG; "Kollidon" is a Trade Mark] in polyethylene glycol of average molecular weight 200, and making up the solution to 3 000 parts by volume with polyethylene glycol of average molecular weight, 200.

(h) The procedure described in (g) above was repeated using 435 parts by weight of the salt, 300 parts by weight of "Kollidon" 12 PF and making up the solution to 3 000 parts by volume with polyethylene glycol of average molecular weight 200.

(i) The procedure described in (g) above was repeated using 435 parts by weight of the salt, 150 parts by weight of "Kollidon" 17 PF [a poly(N-vinylpyrrolidone) having a K value of 17 and available from BASF AG; "Kollidon" is a Trade Mark] and making up the solution to 3 000 parts by volume with polyethylene glycol of average molecular weight 200.

(j) The procedure described in (g) above was repeated using 435 parts by weight of the salt, 300 parts by weight of "Kollidon" 17 PF and making up the solution to 3 000 parts by volume with polyethylene glycol of average molecular weight 200.

(k) The procedure described in (a) above was repeated by dissolving 435 parts by weight of the salt in benzyl alcohol and making up the solution to 3 000 parts by volume with benzyl alcohol.

(l) The procedure described in (a) above was repeated by dissolving 435 parts by weight of the salt in ethyl lactate and making up the solution to 3 000 parts by volume with ethyl lactate.

(m) The procedure described in (a) above was repeated by dissolving 435 parts by weight of the salt and 300 parts by weight of N-(2-hydroxyethyl)lactamide in polyethylene glycol of average molecular weight 200 and making up the solution to 3 000 parts by volume with polyethylene glycol of average molecular weight 200.

EXAMPLE 3

This Example demonstrates the preparation of solutions of the nitroxynil salt of levamisole suitable for parenteral administration in which the salt is formed in situ.

(a) 4-Cyano-2-iodo-6-nitrophenol (19.98 g) was added to a stirred solution of L-2,3,5,6-tetrahydro-6-phenylimidazo[2,1-b]thiazole (14.05 g) in polyethylene glycol of average molecular weight 200 (100 ml) under an atmosphere of nitrogen and the mixture was stirred until homogeneous. The volume of the mixture was made up to 200 ml by the addition of further polyethylene glycol of average molecular weight 200 and the solution obtained was filtered and divided into ampoules in quantities necessary to give a suitable unit dose. The ampoules were sealed and sterilized to give a sterile solution suitable for parenteral injection.

(b) The procedure described in (a) above was repeated substituting polyethylene glycol of average molecular weight 300 for the polyethylene glycol of average molecular weight 200.

(c) The procedure described in (a) above was repeated substituting polyethylene glycol of average molecular weight 400 for the polyethylene glycol of average molecular weight 200.

(d) The procedure described in (a) above was repeated substituting tetrahydrofurfuryl alcohol for the polyethylene glycol of average molecular weight 200.

(e) The procedure described in (a) above was repeated substituting sulfolane for the polyethylene glycol of average molecular weight 200.

(f) The procedure described in (a) above was repeated substituting tetramethylurea for the polyethylene glycol of average molecular weight 200.

(g) The procedure described in (f) above was repeated using half the quantity of tetramethylurea.

(h) The procedure described in (g) above was repeated substituting glycerol formal for tetramethylurea.

EXAMPLE 4

The formulations prepared as described in Examples 2 and 3 above were assessed for tissue reaction at the injection site by injection of a therapeutic dose of the formulations into cattle. The dose rate used was approximately 21 milligrams of active ingredient per kilogram of animal body weight and the injection site was over the third rib of the beast. Assessment of the tissue reaction, if any, were made regularly for a period of up to 21 days after the injection. No unacceptable tissue reactions were noted and after 21 days (N.B. cattle treated with nitroxynil must be withheld from slaughter for a period of 28 days) the type of reaction at each site was rated as follows and are recorded in Table 1 below:

0—No reaction
1—Mild skin thickening and slight swelling of the subcutaneous tissues
2—Similar to 1 but slightly more extensive
4—Swelling up to about 5 cm diameter slightly raised above the body surface
8—Large swelling up to 10 cm in diameter and raised about 5 to 20 mm above body level
16—Larger swelling than 8.

The exponential increase in the rating values takes into account the increasing extent of the irritation. Ratings 0 to 4 inclusive would pass unnoticed in practice. Ratings of 8 and above are noticeable and undesirable. Rating 16 is unacceptable.

TABLE 1

| Tissue Reactions in Cattle after 21 Days | | |
|---|---|---|
| Animal No | Formulation of Example No | Tissue Reaction |
| 1 | 2a | 1 |
| 2 | 2a | 0 |
| 3 | 2a | 0 |
| 4 | 2a | 0 |
| 5 | 2a | 0 |
| 6 | 2b | 1 |
| 7 | 2c | 2 |
| 8 | 2d | 4 |
| 9 | 2e | 1 |
| 10 | 2f | 1 |
| 11 | 2g | 0 |
| 12 | 2h | 0 |
| 13 | 2i | 0 |
| 14 | 2j | 0 |
| 15 | 2k | 0 |
| 16 | 2l | — |
| 17 | 2m | 0 |
| 18 | 3a | 0 |
| 19 | 3a | 0 |
| 20 | 3a | 4 |
| 21 | 3a | 1 |

TABLE 1-continued

| Tissue Reactions in Cattle after 21 Days | | |
|---|---|---|
| Animal No | Formulation of Example No | Tissue Reaction |
| 22 | 3a | 4 |
| 23 | 3a | 1 |
| 24 | 3b | 1 |
| 25 | 3b | 1 |
| 26 | 3c | 1 |
| 27 | 3c | 0 |
| 28 | 3d | 1 |
| 29 | 3d | 1 |
| 30 | 3e | 1 |

EXAMPLE 5

In a test to determine whether the compounds of the present invention, administered parenterally in a single dose, are suitable for the replacement of levamisole and nitroxynil, administered separately as aqueous solutions of levamisole dihydrogen phosphate and nitroxynil N-ethyl-D-glucamine salt respectively, a comparison was made of the levels of levamisole and nitroxynil in the blood of cattle injected with levamisole dihydrogen phosphate, nitroxynil N-ethyl-D-glucamine salt and L-2,3,5,6-tetrahydro-6-phenylimidazo[2,1-b]thiazolium 4-cyano-2-iodo-6-nitrophenoxide.

In the test each of four cattle were injected with an aqueous solution of levamisole dihydrogen phosphate at a dose rate equivalent to 6 milligrams of levamisole per kilogram of animal body weight. Blood samples were taken from the animals 1 hour, 2 hours, 4 hours and 24 hours after injection and the levamisole content of the blood was determined using high pressure liquid chromatography. In each of the four animals the level of levamisole in the blood reached a maximum within 1 hour of the injection and had reduced to approximately 25% of the maximum level within 4 hours of the injection.

The above test was repeated by injecting another four cattle with an aqueous solution of nitroxynil N-ethyl-D-glucamine salt at a dose rate equivalent to 10 milligrams of nitroxynil N-ethyl-D-glucamine salt per kilogram of animal body weight. Blood samples were taken from the animals 1 hour, 2 hours, 4 hours and 24 hours after injection and the nitroxynil content of the blood was determined using high pressure liquid chromatography. In each of the four animals the level of nitroxynil in the blood reached a maximum 4 hours after the injection and remained close to that maximum level for at least 24 hours.

The above test was repeated by injecting another four cattle with a solution of L-2,3,5,6-tetrahydro-6-phenylimidazo[2,1-b]thiazolium 4-cyano-2-iodo-6-nitrophenoxide in polyethylene glycol of average molecular weight 200 prepared as described in Example 2 (a) above, at a dose rate equivalent to 17 milligrams of the salt per kilogram of animal body weight. Blood samples were taken from the animals 1 hour, 2 hours, 4 hours and 24 hours after injection and the levamisole content and the nitroxynil content of the blood was determined using high pressure liquid chromatography. In each of the four animals the level of levamisole in the blood reached a maximum approximately 2 hours after injection and still remained at at least 50% of the maximum level 4 hours after the injection. In each of the four animals the level of nitroxynil in the blood reached a maximum approximately 24 hours after the injection.

The result of the comparative study showed that therapeutic levels of levamisole and nitroxynil can be obtained in the blood of animals by parenteral administration of L-2,3,5,6-tetrahydro-6-phenylimidazo[2,1-b]thiazolium 4-cyano-2-iodo-6-nitrophenoxide. Moreover, the results also showed that the blood levels of both levamisole and nitroxynil rose to a maximum much more slowly in animals injected with L-2,3,5,6-tetrahydro-6-phenylimidazo[2,1-b]thiazolium 4-cyano-2-iodo-6-nitrophenoxide than in animals injected with levamisole dihydrogen phosphate and nitroxynil N-ethyl-D-glucamine salt respectively. The results also showed that in comparison to parenteral administration of levamisole dihydrogen phosphate, the parenteral administration of L-2,3,5,6-tetrahydro-6-phenylimidazo[2,1-b]thiazolium 4-cyano-2-iodo-6-nitrophenoxide has the advantage that the level of levamisole in the blood of the treated animal is maintained for a longer period of time.

EXAMPLE 6

This Example demonstrates the anthelmintic efficacy of the compounds of the present invention.

To ensure that the compounds were tested in heavily infected animals sheep harbouring a heavy naturally acquired parasitic infection were chosen and further infected with larvae of the species Ostertagia, Trichostrongylus and Haemonchus. The infections were allowed to reach maturity. One group of sheep were injected with a solution of L-2,3,5,6-tetrahydro-6-phenylimidazo[2,1b]thiazolium 4-cyano-2-iodo-6-nitrophenoxide in polyethylene glycol of average molecular weight 200 at a dose rate equivalent to 14.5 mg of the salt per kilogram of animal body weight. A second group of sheep, the controls, were injected with an aqueous solution of levamisole dihydrogen phosphate at a dose rate equivalent to 6 mg of levamisole base per kilogram of animal body weight.

Half of the sheep in each group were slaughtered 7 days after treatment and the parasites in the abomasum, small intestine, large intestine and lungs were counted. In each case slaughter showed that both the compound of the invention and the control compound had either completely or essentially completely eradicated the helminth infection.

To establish that all eggs and immature helminths had been killed by the treatment the other half of the sheep in each group were slaughtered 28 days after treatment and the parasites in the abomasum, small intestine, large intestine and lungs were counted. Again in each case slaughter showed that both the compound of the invention and the control compound had either completely or essentially completely eradicated the helminth infection.

I claim:

1. A compound selected from D,L-2,3,5,6-tetrahydro-6-phenylimidazo[2,1-b]thiazolium 4-cyano-2-iodo-6-nitrophenoxide and L-2,3,5,6-tetrahydro-6-phenylimidazo[2,1-b]thiazolium 4-cyano-2-iodo-6-nitrophenoxide.

2. The compound L-2,3,5,6-tetrahydro-6-phenylimidazo[2,1-b]thiazolium 4-cyano-2-iodo-6-nitrophenoxide.

3. A composition comprising as active ingredient a compound as defined according to claim 1 and a pharmaceutically acceptable carrier therefor.

4. A composition in the form of a sterile solution suitable for parenteral administration comprising from 5 to 70% by weight of L-2,3,5,6-tetrahydro-6-phenylimidazo[2,1-b]thiazolium 4-cyano-2-iodo-6-nitrophenoxide in a pharmaceutically acceptable solvent.

5. A composition according to claim 4 wherein said solvent is selected from the group consisting of: alcohols; ketones; ester; amides; sulfoxides; sulfones; cyclic ethers; formals; hydrocarbons; perfluorinated hydrocarbons; glycols and glycol derivatives; pyrrolidones; silicone oils; aprotic solvents; and mixtures thereof.

6. A composition according to claim 5 wherein said solvent is selected from the group consisting of: benzyl alcohol; tetrahydrofurfuryl alcohol; ethyl lactate; N-(2-hydroxyethyl)lactamide; dimethylsulfoxide; sulfolane; glycerol formal; perfluorodecalin; propylene glycol; polyethylene glycols; diethylene glycol dimethyl ether; N-methylpyrrolidone; poly(N-vinylpyrrolidone); polymethylsiloxane; dimethylformamide; dimethylacetamide; tetramethylurea; and mixtures thereof.

7. A sterile injectable composition comprising from 5 to 30% by weight of L-2,3,5,6-tetrahydro-6-phenylimidazo[2,1-b]thiazolium 4-cyano-2-iodo-6-nitrophenoxide in a solvent selected from the group consisting of: benzyl alcohol; ethyl lactate; polyethylene glycol of averagle molecular weight in the range of from 100 to 600; poly(N-vinylpyrrolidone); and mixtures thereof.

8. A sterile injectable solution according to claim 7 comprising from 10 to 20% by weight of L-2,3,5,6-tetrahydro-6-phenylimidazo[2,1-b]thiazolium 4-cyano-2-iodo-6-nitrophenoxide in polyethylene glycol of average molecular weight in the range of from 200 to 400.

9. A process for killing internal parasites of warm blooded animals which process comprises treating the infected animal with a therapeutically effective amount of a compound as defined according to claim 1.

10. A process for killing internal parasites of warm blooded animals which process comprises treating the infected animal with a therapeutically effective amount of a composition as defined according to claim 3.

11. A process for killing internal parasites of warm blooded animals which process comprises parenteral administration to the infected animal of a therapeutically effective amount of a composition as defined according to claim 3.

12. A process according to claim 11 wherein said compound is administered at a dose rate in the range of from 10 to 25 milligrams per kilogram of animal body weight.

13. A process according to claim 12 wherein the dose rate is in the range of from 12 to 17 milligrams per kilogram.

14. A process according to claim 9 wherein said warm blooded animals are sheep or cattle.

* * * * *